United States Patent [19]

Bywater

[11] Patent Number: 4,707,474
[45] Date of Patent: Nov. 17, 1987

[54] VETERINARY COMPOSITION OF CLOXACILLIN FOR EYE TREATMENT

[75] Inventor: Robert J. Bywater, Tadworth, England

[73] Assignee: Beecham Group p.l.c., England

[21] Appl. No.: 492,472

[22] Filed: May 6, 1983

[30] Foreign Application Priority Data

May 12, 1982 [GB] United Kingdom ................ 8213703

[51] Int. Cl.$^4$ ............................................. A61K 31/43
[52] U.S. Cl. ........................................................ 514/196
[58] Field of Search ........................ 424/271; 514/196

[56] References Cited

U.S. PATENT DOCUMENTS

| | | | |
|---|---|---|---|
| 2,792,329 | 5/1957 | Woodard | 424/271 |
| 3,549,746 | 12/1970 | Granatek | 424/271 |
| 3,996,355 | 12/1976 | Lin et al. | 424/271 |
| 4,073,920 | 2/1978 | Dowrick | 424/271 |
| 4,079,138 | 3/1978 | Lin et al. | 424/246 |

FOREIGN PATENT DOCUMENTS 0010904 10/1979 European Pat. Off. .
1547164 8/1975 United Kingdom .

*Primary Examiner*—Stanley J. Friedman
*Attorney, Agent, or Firm*—Jacobs & Jacobs

[57] ABSTRACT

Compositions comprising a cloxacillin salt and liquid paraffin, arachis oil or fractionated coconut oil are useful in treating infectious keratoconjunctivitis in cattle and domestic animals.

21 Claims, No Drawings

VETERINARY COMPOSITION OF CLOXACILLIN FOR EYE TREATMENT

This invention relates to a method for the treatment of infectious keratoconjunctivitis in animals.

Infectious keratoconjunctivitis in animals is a particularly distressing condition. Infectious bovine keratoconjunctivitis (IBK), for example, is a highly contagious disease of cattle caused by *Moraxella bovis*. The cattle disease causes economic loss, through slower growth of calves; slower weight gain in feeder cattle, reduced milk yield from cows, and treatment costs, as well as eye disfigurement and blindness. It is known to use antibiotics and other medicaments in the treatment of infectious keratoconjunctivitis. Previously, the various recommended treatments have required repeated application of the medicament because of their short duration of action which is both inconvenient and leads to a risk of incomplete treatment.

Whilst a number of antibiotics have been used in the treatment of infectious keratoconjunctivitis, the sodium salt of 3-o-chlorophenyl-5-methyl-4-isoxazolyl penicillin (sodium cloxacillin), a well known, broad spectrum antibiotic, has been said to be contra-indicated for opthalmic use. This follows from reports that it produced opacity of the cornea of rabbits when administered, by subconjuntual injection into the eye, as a 50% solution; the opacity was found to persist for at least 14 days with only a slight decrease in intensity [Nature, 1962, 195, 1264, see also Veterinary Applied Pharmacology and Therapeutics, G. C. Brander and D. M. Pugh, Baillière Tindall-London, Second Edit.n, 1971, page 320].

Surprisingly, we have now discovered that certain formulations of a salt of cloxacillin and a veterinarily acceptable oil as carrier, which are known for the treatment of bovine mastitis provide prolonged inhibitory levels of antibiotic and are useful in a safe, 'once only' method of treatment of infectious keratoconjunctivitis in animals.

According to the present invention there is provided a method for the treatment of infectious keratoconjunctivitis in animals, which comprises administering to the animal by topical instillation, a formulation comprising a salt of cloxacillin and a veterinarily acceptable oil as carrier. The invention is especially applicable in the treatment of Bovine infectious keratoconjunctivitis.

The formulations suitably contain sodium or benzathine cloxacillin in an oil base. Typically, the concentration of cloxacillin salt is from 10 to 30% by weight of the formulation. Suitably, the oil base is a mineral oil base, preferably liquid paraffin containing from 0 to 5% by weight of composition of aluminium stearate and from 0 to 2% by weight of composition of stearic acid, or a vegetable oil such as arachis oilor a fractionated coconut oil (such as a Miglyol or Neobee). Particularly suitable for the present invention are formulations of cloxacillin such as those described in UK Patent Specification Nos. 1312918, 1455296, 1547164, and European Patent Specifications Nos. 0010904 and 0010903.

A number of known containers suitable for instillation of the formulation onto an infected eye may be used. Preferably, the container is a sealed aluminium tube, or a polyethylene syringe.

The dosage regimes will vary according to the size of the sufferer. A suitable dosage unit is generally between 20 to 200 mg of cloxacillin salt. For the treatment of cattle, a dose of about 125 mg of cloxacillin salt is appropriate. A smaller dose, such as about 50 mg, is suitable in the treatment of domestic animals, such as dogs or cats.

The treatment will, in most cases, require a single application of the formulation, however severe infections may require more than one application.

The following Example illustrates the invention.

EXAMPLE

An ointment formulation was aseptically prepared from:

| | | % by weight of composition |
|---|---|---|
| cloxacillin benzathine | | 16.67 |
| liquid paraffin | } Mineral Oil Base | 80.10 |
| aluminium stearate | | 2.56 |
| stearic acid | | 0.67 |
| | | 100.00 |

The mineral oil base was prepared by mixing aluminium stearate, stearic acid and some of the liquid paraffin. This dispersion was then mixed with a further quantity of heated liquid paraffin followed by the remaining liquid paraffin. The mixture was heat sterilised, cooled, stirred then transferred into a sterile manufacturing area.

In the sterile manufacturing area, sterile milled cloxacillin benzathine was dispersed in the sterile mineral oil base. The suspension so formed was then milled, mixed, milled again and remixed to achieve homogeneity.

The suspension was packaged into 1 ml polyethylene syringes or aluminium tubes; this constituted a single dose form containing 125 mg of cloxacillin benzathine BP suitable for the treatment of bovine infectious keratoconjunctivitis.

Biological Evaluation

The following tests were undertaken to establish the efficacy of the above formulation and lack of undesirable side effects.

A. Test for the duration of therapeutic concentrations

A single dose was instilled beneath the lower eyelids of eight cows. Samples of lachrymal fluid were taken at ½, 1, 2, 4, 6, 8 and 24 hours after instillation using 6 mm diameter filter paper discs left in the corner of the eye for 20 seconds to become saturated. Sample discs were then weighed against saturated replicas to confirm complete saturation. Microbiological assay was then used to determine the antibiotic concentrations using *Bacillus subtilis* for cloxacillin. The results are presented in Table 1.

TABLE 1

Mean antibiotic concentrations in lachrymal fluid following single topical instillations of benzathine cloxacillin in mineral oil base.

| | | Benzathine cloxacillin in mineral oil base 125 mg dose |
|---|---|---|
| Mean Antibiotic | ½ | 799 ± 268 |
| Concentrations | 1 | 623 ± 282 |
| (µg/ml) per time | 2 | 631 ± 336 |
| interval (hrs) | 4 | 471 ± 284 |
| after instillation | 6 | 357 ± 264 |
| (n = 8) | 8 | 187 ± 144 |
| | 24 | 78.5 ± 92.2 |
| | 36 | 10.4 ± 10.7 |
| | 48 | 4.7 ± 5.2 |
| | 56 | 4.1 ± 3.3 |

TABLE 1-continued

Mean antibiotic concentrations in lachrymal fluid following single topical instillations of benzathine cloxacillin in mineral oil base.

| | Benzathine cloxacillin in mineral oil base 125 mg dose |
|---|---|
| 72 | 2.0 ± 2.2 |
| 86 | 1.5 ± 1.5 |

Therapeutic concentrations persisted for at least 56 hours.

B. In vitro determination of minimum inhibitory concentrations (mic) of cloxacillin to field strains of *Moraxella bovis*

Strains of *Moraxella bovis* were accumulated and mic's were determined for cloxacillin using the method described by Ericsson, H. M. and Sherris, J. C. in 'Antibiotic Sensitivity Testing', Report of International Collaborative Study, Acta Pathol et Microbiol Scand, Section B, Supplement 217 (1971).

Minimum inhibitory concentrations (mics) for cloxacillin were determined for a number of isolates of *Moraxella bovis* obtained from various sources. The results are shown in Table 2.

TABLE 2

Minimum inhibitory concentrations of cloxacillin to field isolates of *Moraxella bovis*.

| | *Moraxella bovis* | | | |
|---|---|---|---|---|
| Concentrations Cloxacillin m.i.c. mg/ml | 0.31 | 0.62 | 1.25 | 2.5 |
| No of isolates = 44 | 5 | 18 | 15 | 6 |

The incidence of *Moraxella bovis* pre- and post treatment in the eyes of 20 cattle was also determined; the results are shown in Table 3.

TABLE 3

| Clinical condition of eyes | Moraxella isolation (%) |
|---|---|
| Clinically normal eyes | 7/16 (44%) |
| Affected eyes pre-treatment | 15/18 (83%) |
| Affected eyes post treatment | 3/7 (43%) |

D. The clinical response to treatment by a 125 mg dose of cloxacillin in 20 cases of IBK is shown in Table 4.

TABLE 4

Mean time taken for resolution of clinical parameters following a single topical instillation of 125 mg cloxacillin.

| Combined clinical conditions present in 20 cattle | Time (days) to effect clinical resolution ± SD |
|---|---|
| Lachrymation - slight/moderate/perfuse n = 22 | 1.5 ± 0.8 |
| Blepharospasm - eyelids fully or ¾ closed to ¼ or fully open n = 22 | 2.0 ± 1.4 |
| Corneal ulceration to heal n = 22 | 7.0 ± 4.0 |

E. Irritation Study

Benzathine cloxacillin was liberally instilled into the right eyes of nine heifers on five consecutive days and then repeated on a single occasion after ten days. The latter infusion was carried out to investigate the possibility of induced hypersensitivity. All left eyes were designated as untreated controls. After instillation, all eyes were clinically examined twice daily using a bright light source for the possible detection of changes in corneal transparency, degree of lachrymation and the presence of blepharospasm or conjunctival inflammation. In addition, corneal/conjunctival smears were taken daily onto glass slides and stained with methylene blue. Numbers of nucleated epithelial cells were then recorded over a standard number of microscope fields and numerical comparison made between treated and untreated eyes.

Repeated infusion gave no sign of irritation or change in the cornea, nor was there any change in the epithelial cells present.

The concentrations obtained by a single topical application appeared to remain above the mic for *Moraxella bovis* for 2-3 days, showing that a single application is clinically effective. This was confirmed by a limited field trial. Between the months of July and September, a small field trial was carried out on three farms in young cattle. Twenty clinically infected animals were selected having a combination of excessive lachrymation, blepharospasm and ulcerated cornea, the latter assessed by the uptake of fluorescein. These three conditions were graded according to their severities. Swabs were taken from both eyes at the initial examination and were subjected to bacteriological diagnosis. All clinically infected eyes were then treated with 125 mg doses of benzathine cloxacillin instilled beneath the lower eyelids. The treated cattle showed a rapid response in terms of lachrymation and blepharospasm. The healing of the corneas took somewhat longer, but this is to be expected.

It is concluded that a single topical application of benzathine cloxacillin is an effective treatment for IBK.

I claim:

1. A method for treating infectious keratoconjunctivitis of animals comprising administering an effective, non-toxic amount of a formulation comprising an effective amount of a veterinarily acceptable cloxacillin salt and a veterinarily acceptable oil, by instillation into an infected eye of the animal.

2. A method according to claim 1 wherein the formulation comprises sodium or benzathine cloxacillin.

3. A method according to claim 1 wherein the formulation comprises from 10 to 30% by weight said cloxacillin salt.

4. A method according to claim 1 wherein the oil is liquid paraffin or a vegetable oil.

5. A method according to claim 4 wherein the oil is liquid paraffin containing from 0 to 5% by weight of the composition of aluminum stearate and from 0 to 2% by weight of the composition of stearic acid.

6. A method according to claim 4 wherein the oil is a vegetable oil selected from arachis oil and fractionated coconut oil.

7. A method according to claim 1 wherein from 20 to 200 mg of cloxacillin salt is administered to the infected eye.

8. A method according to claim 1 wherein the animal is bovine.

9. A method according to claim 1 wherein about 125 mg of cloxacillin salt is administered to an infected eye of a bovine.

10. A method according to claim 1 wherein the animal is a domestic animal.

11. A method according to claim 1 wherein the animal is a cat or dog.

12. A method according to claim 1 wherein about 50 mg said cloxacillin salt, is administered to an infected eye of a cat or dog.

13. A method according to claim 7, wherein said formulation comprises from 10 to 30% by weight of said cloxacillin salt, and said oil is liquid paraffin or a vegetable oil.

14. A method according to claim 13, wherein the oil is liquid paraffin containing from 0 to 5% by weight of the composition of aluminum stearate and from 0 to 2% by weight of the composition of stearic acid.

15. A method according to claim 13 wherein the oil is a vegetable oil selected from arachis oil and fractionated coconut oil.

16. A method according to claim 8, wherein said formulation comprises from 10 to 30% by weight of said cloxacillin salt, and said oil is liquid paraffin or a vegetable oil.

17. A method according to claim 16, wherein the oil is liquid paraffin containing from 0 to 5% by weight of the composition of aluminum stearate and from 0 to 2% by weight of the composition of stearic acid.

18. A method according to claim 16, wherein the oil is a vegetable oil selected from arachis oil and fractionated coconut oil.

19. A method according to claim 11, wherein said formulation comprises from 10 to 30% by weight of said cloxacillin salt, and said oil is liquid paraffin or a vegetable oil.

20. A method according to claim 19, wherein the oil is liquid paraffin containing from 0 to 5% by weight of the composition of aluminum stearate and from 0 to 2% by weight of the composition of stearic acid.

21. A method according to claim 20, wherein the oil is a vegetable oil selected from arachis oil and fractionated coconut oil.

* * * * *